(12) United States Patent
Kim et al.

(10) Patent No.: US 7,695,608 B2
(45) Date of Patent: Apr. 13, 2010

(54) ELECTROCHEMICAL BIOSENSOR AND BIOSENSOR MEASURING DEVICE

(75) Inventors: Keun Ki Kim, Seoul (KR); Jae Hyun Yoo, Seoul (KR); Gang Cui, Seoul (KR); Moon Hwan Kim, Seoul (KR); Hakhyun Nam, Seoul (KR); Geun Sig Cha, Seoul (KR)

(73) Assignee: i-SENS, Inc., Seoul (KR)

( * ) Notice: Subject to any disclaimer, the term of this patent is extended or adjusted under 35 U.S.C. 154(b) by 399 days.

(21) Appl. No.: 11/747,945

(22) Filed: May 14, 2007

(65) Prior Publication Data

US 2008/0237062 A1    Oct. 2, 2008

(30) Foreign Application Priority Data

Mar. 28, 2007    (KR) .................. 10-2007-0030346

(51) Int. Cl.
*G01N 27/403*    (2006.01)
*G01N 27/327*    (2006.01)
*G01N 21/00*    (2006.01)
*G06K 9/36*    (2006.01)
*G03B 7/08*    (2006.01)

(52) U.S. Cl. .............. 205/775; 205/777.5; 204/403.02; 422/55; 235/462.09; 235/462.24

(58) Field of Classification Search ................................. 204/403.01–403.15, 400; 205/777.5, 778, 205/792, 775; 422/55–58; 235/462.01, 462.09, 235/462.24
See application file for complete search history.

(56) References Cited

U.S. PATENT DOCUMENTS 3,907,503 A    9/1975  Betts et al.
4,510,383 A *  4/1985  Ruppender ............. 235/462.21
5,266,179 A * 11/1993  Nankai et al. ................ 204/401

(Continued)

OTHER PUBLICATIONS

JPO abstract for JP 02175194 A, patent published on Jul. 6, 1990.*
Bauman et al., Preparation of Immobilized Cholinesterase for Use in Analytical Chemistry, Analytical Chemistry, 1965, 1378-1381 vol. 37, No. 11, Midwest Research Institute, Kansas City.
Oldham, Steady-State Voltammetry, Microelectrodes: Theory and Applications, 35-50, 1991 Kluwer Academic Publishers, Printed in the Netherlands.
Cassidy et al., Novel Electrochemical Device for the Detection of Cholesterol or Glucose, Analyst, 415-418, 1993, vol. 118, Ireland.

*Primary Examiner*—Alex Noguerola
(74) *Attorney, Agent, or Firm*—Bachman & LaPointe, P.C.

(57) ABSTRACT

An electrochemical biosensor and a biosensor measuring device. The electrochemical biosensor includes a plurality of electrodes, capillary sample cell portions, reaction reagent layers, electrode connection portions, and a production lot information identification portion. The production lot information identification portion is configured such that the production lot information is recorded thereon has one or more infrared absorption/reflection marks, which indicate information about differences between production lots through the printing and/or attachment of colored or colorless materials, having differences in absorbency or reflectivity of infrared rays, in conformity of a predetermined pattern or through the attachment of transparent films. The electrochemical biosensor measuring device includes a plurality of integrated photoreflector sensing devices that emit and receive infrared rays to identify the production lot information recorded on the production lot information identification portion of the biosensor.

9 Claims, 3 Drawing Sheets

U.S. PATENT DOCUMENTS

| | | |
|---|---|---|
| 5,597,532 A | 1/1997 | Connolly |
| 5,741,634 A * | 4/1998 | Nozoe et al. ............ 204/403.03 |
| 5,945,341 A | 8/1999 | Howard, III |
| 5,989,917 A | 11/1999 | McAleer et al. |
| 6,168,957 B1 | 1/2001 | Matzinger et al. |
| 6,458,258 B2 * | 10/2002 | Taniike et al. .......... 204/403.14 |
| 6,770,487 B2 | 8/2004 | Crosby |
| 6,814,844 B2 | 11/2004 | Bhullar et al. |
| 2005/0279647 A1 | 12/2005 | Beaty |
| 2006/0144704 A1 | 7/2006 | Ghesquiere et al. |
| 2007/0015286 A1 | 1/2007 | Neel et al. |

\* cited by examiner

ELECTROCHEMICAL BIOSENSOR AND BIOSENSOR MEASURING DEVICE

BACKGROUND OF THE INVENTION

1. Field of the Invention

The present invention relates to an electrochemical biosensor and a biosensor measuring device.

2. Description of the Related Art

For the diagnosis and prophylaxis of diabetes mellitus, the importance of periodic monitoring of blood glucose levels has been increasingly emphasized. Nowadays, strip-type biosensors designed for hand-held reading devices allow individuals to readily monitor glucose levels in blood.

A large number of commercialized biosensors measure blood glucose present in blood samples using an electrochemical technique. The principle of the electrochemical technique is based on the following Reaction 1.

$$\text{Glucose} + \text{GO}_x\text{-FAD} \rightarrow \text{gluconic acid} + \text{GOx-FADH}_2$$

$$\text{GO}_x\text{-FADH}_2 + M_{ox} \rightarrow \text{GOx-FAD} + M_{red} \quad \text{[Reaction 1]}$$

wherein, $\text{GO}_x$ represents glucose oxidase; $\text{GO}_x\text{-FAD}$ and $\text{GO}_x\text{-FADH}_2$ respectively represent an oxidized and a reduced state of glucose-associated FAD (flavin adenine dinucleotide), a cofactor required for the catalyst of glucose oxidase; and $M_{ox}$ and $M_{red}$ denote an oxidized and a reduced state of an electron transfer mediator, respectively.

The electrochemical biosensor uses organic electron transfer materials, such as ferrocenes or their derivatives, quinines or their derivatives, organic or inorganic materials containing transition metals (hexaamine ruthenium, polymer containing osmium, potassium ferricyamide and the like), organic conducting salts, and viologens, as electron transfer mediators.

The principle of measuring blood glucose by the biosensor is as follows.

glucose in blood is oxidized to gluconic acid by the catalysis of the glucose oxidase, with the cofactor FAD reduced to $\text{FADH}_2$. Then, the reduced cofactor $\text{FADH}_2$ transfers electrons to the mediator, so that $\text{FADH}_2$ returns to its oxidized state; that is, FAD and the mediator are reduced. The reduced mediator is diffused to the surface of the electrodes. The series of reaction cycles is driven by the anodic potential applied at the working electrode, and the redox current proportional to the level of glucose is measured.

Compared to biosensors based on colorimetry, the electrochemical biosensors (e.g., based on electrochemistry) has the advantages of being not influenced by oxygen and allowing the use of samples, even if cloudy, without pretreatment thereof.

Although this electrochemical biosensor is generally conveniently used to monitor and control the amount of blood glucose, its accuracy is greatly dependent on deviations according to each mass-production lot in which the biosensors are produced. In order to eliminate this deviation, most of the commercialized biosensors are designed such that a user directly inputs calibration curve information, which is predetermined at the factory, into a measuring device capable of reading the biosensor. However, this method causes the user inconvenience and causes the user to make an input error, thus inaccurate results can be acquired.

In order to solve such a problem, a method that can adjust the resistance of each electrode such that production information for each lot is stored at a location at which contact of the electrode of a sensor is made (US20060144704A1), a method in which a conductor is printed in a bar code type (U.S. Pat. No. 6,814,844), a method in which a connection to a resistor bank is made (WO2007011569A2), and a method that reads information by varying resistance through adjustment of length or thickness of each electrode (US20050279647A1) have been proposed. The methods proposed for the electrochemical biosensors are all based on a technique capable of reading electrical variation. Furthermore, a method that discriminates production lot information by reading the resistivity of a conductor marked on a strip using an electrical method (U.S. Pat. No. 4,714,874) has been proposed.

However, these methods are methods that accurately adjust resistance, and must undergo a process of mass-producing the sensors first, measuring statistical characteristics of the sensors, and post-processing the measured information again using a method of adjusting the resistance marked on the sensors. However, the process of accurately adjusting the resistance, marked in large quantities, through the post-process is very inconvenient, and is difficult to use for practical application.

Methods in which colored marks are used to enable a spectral system capable of discriminating colors to use a colorimetric method (U.S. Pat. Nos. 3,907,503, 5,597,532, 6,168,957), and a method in which a plurality of color marks is read at various wavelengths of visible and infrared ray regions using a spectroscope (U.S. Pat. No. 5,945,341), and a method capable of reading bar codes (EP00075223B1, WO02088739A1) have been proposed. These methods using color or bar code are favorable for a calorimetric method-based sensor using the spectrum system, but they have technical and economic difficulties in being applied to the system using an electrochemical measurement mechanism. For example, the size and structure of a portion where the electrochemical sensor strip is inserted into the measuring device for the purpose of electrical connection, that is, a connection space of the sensor strip, is very limited in constructing a device and circuit for spectroscopically identifying a structure into which the production lot information is input. Further, a process of scattering and identifying various wavelengths of light detected by a detector is required to discriminate color, and a process of converting an analog signal into a digital signal and performing calculation is complicated, so that the device and its program are complicated, therefore the expense for constructing the system is greatly increased.

Furthermore, instead of the methods of marking the production lot information on the sensor strip, a method of recording information on a container or pack containing a sensor and allowing the information to be read by the measuring device (EP0880407B1) has been proposed. However, this method also has a possibility of causing the user to make an error of incorrectly reading a code recorded on the container.

For these reasons, the inventors of the present invention have conducted research into electrochemical biosensors in order to maintain economic efficiency in the construction of the measuring device while allowing the mass production of the electrochemical biosensor, which allows the production lot information thereof to be easily and accurately input into the measuring device without the mistake of the user and thus provides an accurate measurement value. In the process of the research, it has been found that, when the production lot information is recorded on the electrochemical biosensor strip using infrared absorption/reflection marks and when a production lot information identification portion at which the production lot information is recorded on the electrochemical biosensor strip is identified in the measuring device, there is no need to use a high-priced filter in the case where surface mounted miniaturized integrated infrared photo-reflector sensing devices in which light-emitting units (light emitters), that is, infrared emitting diodes, and light-receiving units (detectors), that is, photodiodes, are disposed in the same direction, are used in an integrated light-emitter and detector system in one component chip (hereafter called, photo-reflector), so that the light emitter-detector system has a simple construction on the same printed circuit board (PCB) of measuring device, and thus can not only reduce a complicated calculation process performed for post-treatment but also maintain economic efficiency in the construction of the measuring device. As a result, the present invention was completed.

SUMMARY OF THE INVENTION

Accordingly, the present invention has been made keeping in mind the above problems occurring in the prior art, and an object of the present invention is to provide an electrochemical biosensor, and a biosensor measuring device having photo-reflector sensing devices, which, when the electrochemical biosensor is inserted into the measuring device without the mistake of a user, automatically identifies production lot information of the biosensor, thus enabling blood glucose to be conveniently and accurately measured and being economical.

In order to accomplish the above object, the present invention provides an electrochemical biosensor prepared on at least two insulating plates, comprising: a plurality of electrodes, capillary sample cell, reaction reagent layers, electrical connection portions; and a production lot information identification portion configured such that production lot information is recorded on at least one insulating plate; wherein the production lot information identification portion configured such that the production lot information is recorded thereon has infrared absorption/reflection marks, which indicate information about differences between production lots through printing of colored or colorless materials or attachment of transparent films, having differences in absorbency or reflectivity of infrared rays, in conformity of a predetermined pattern.

In addition, the present invention provides an electrochemical biosensor measuring device quantitatively determining analytes using the electrochemical biosensor, wherein the electrochemical biosensor measuring device, comprising a plurality of integrated photo-reflector sensing devices that emit and receive reflected infrared rays in one component chip mounted on the same PCB of electrochemical measuring device to identify the infrared absorbing/reflecting production lot information recorded on the production lot information identification portion of the biosensor.

In the present specification, the term 'biosensor' is used as having the same meaning as the term 'biosensor strip.'

BRIEF DESCRIPTION OF THE DRAWINGS

The above and other objects, features and advantages of the present invention will be more clearly understood from the following detailed description taken in conjunction with the accompanying drawings, in which.

BRIEF DESCRIPTION OF THE MARK OF DRAWINGS

Figure 1:
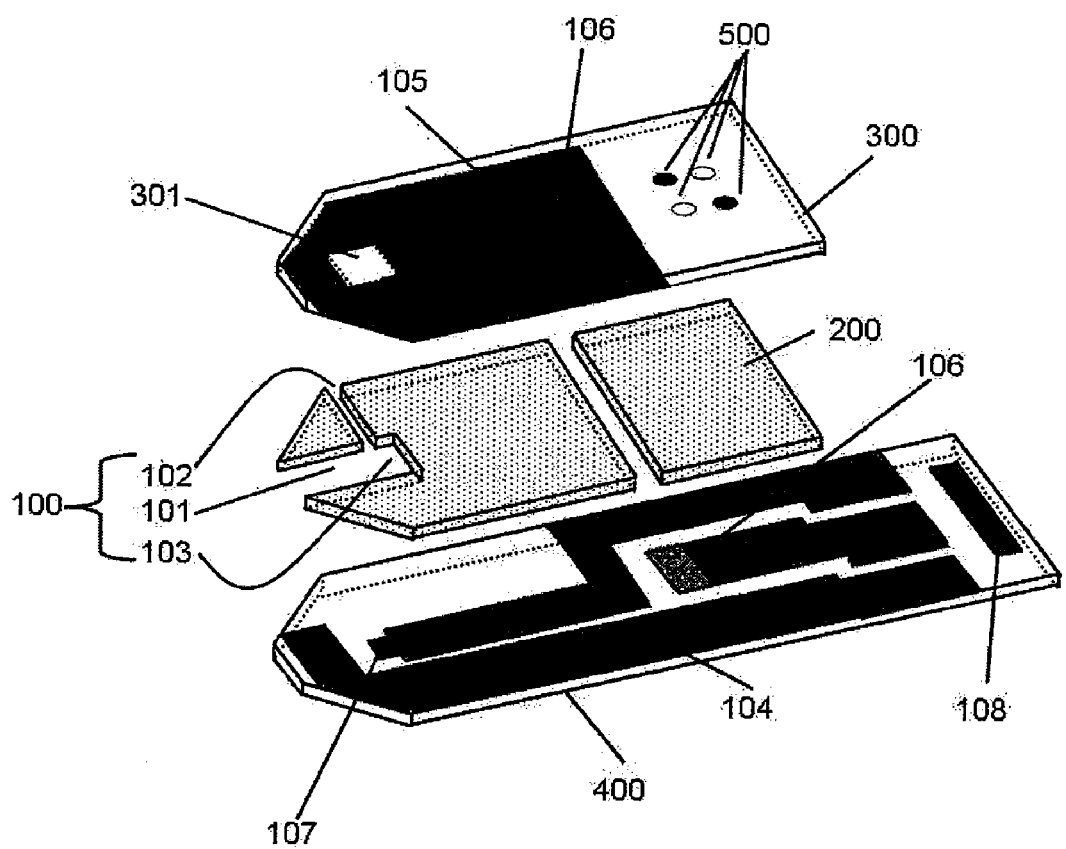
FIG. 1 is an exploded view of a biosensor, in which production lot information indicated by infrared absorption/reflection marks is recorded in the upper plate thereof, according to an embodiment of the present invention.

101: sample introducing pass
102: air vent
103: allowance space portion
104: working electrode
105: auxiliary electrode
106: electrode connection portion
107: flow sensing electrode
108: biosensor confirming electrode
200: middle plate
300: upper plate
400: lower plate
500: production lot information identification portion
700: sensor connector
702: near infrared light-emitting unit
703: near infrared light-receiving unit
704: Printed Circuit Board
705: electrical connection portion

DESCRIPTION OF THE PREFERRED EMBODIMENTS

The present invention provides an electrochemical biosensor prepared on at least two insulating plates, comprising: a plurality of electrodes, capillary sample cell, reaction reagent layers, electrical connection portions; and a production lot information identification portion configured such that production lot information is recorded on at least one insulating plate; wherein the production lot information identification portion configured such that the production lot information is recorded thereon has infrared absorption/reflection marks, which indicate information about differences between production lots through printing of colored or colorless materials or attachment of transparent films, having differences in absorbency or reflectivity of infrared rays, in conformity of a predetermined pattern.

The present invention is described in detail below.

The present invention provides an electrochemical biosensor, including an electrode pattern comprising a working electrode and an auxiliary electrode that are respectively formed on at least two planar insulating plates; a fine flow pass sample cell portion configured to guide a liquid sample to the electrode pattern; a reaction reagent layer comprising enzyme and an electron transfer mediator on the working electrode; electrode connection portions used to connect the working electrode and the auxiliary electrode; and a production lot information identification portion configured such that production lot information is recorded on at least one insulating plate, which is selected from among at least two planar insulating plates and does not interrupt connection between the electrodes; wherein the production lot information identification portion configured such that the production lot information is recorded has one or more infrared absorption/reflection marks, which indicate information about differences between production lots through the print of colored or colorless materials, having differences in absorbency or reflectivity of infrared rays, in conformity of a predetermined pattern or through the attachment of transparent films.

The electrode pattern of the electrochemical biosensor according to the present invention may be formed on one or both of at least two planar insulating plates. That is, (1) a single working electrode and a single auxiliary electrode (or reference electrode) may be formed on the same planar insulating plate, or (2) may be formed on two planar insulating plates to be arranged opposite one another [counter-type electrodes; reference: E. K. Bauman et al., Analytical Chemistry, vol 37, p 1378, 1965; K. B. Oldham in "Microelectrodes: Theory and Applications," Kluwer Academic Publishers, 1991; J. F. Cassidy et al., Analyst, vol 118, p 415].

Furthermore, the electrode pattern of the electrochemical biosensor according to the present invention may further include a flow sensing electrode that is disposed behind the working electrode and is capable of measuring the fluidity of whole blood samples on a lower planar insulating plate.

The counter-type electrodes are described in greater detail by way of example of the biosensor.

In the case where the electrochemical biosensor used for the electrochemical biosensor measuring device according to the present invention is constructed using the counter-type electrodes, the working electrode and the auxiliary electrode may be formed to have a structure in which the electrodes are isolated by a pressure adhesive isolation plate having a thickness of 50~250 μm at a symmetrically or non-symmetrically opposite location.

The isolation plate has a fine flow pass sample cell portion, the unit of the total volume of which is microliter, so that a bionic sample can be injected into a measurement space, which is formed by the working electrode and the auxiliary electrode, and be retained therein. The sample cell portion includes a sample introducing portion 100 and a fine flow pass.

When electrodes are formed, a flow sensing electrode in the isolation plate is spaced apart from the working electrode or the auxiliary electrode by an appropriate distance. It is preferred that the flow sensing electrode be located at a distance at which blood, wherein the blood has a total cell volume of 40% and has been treated with fluoride, can travel within about 600 ms the entire fine flow pass having a width of 0.5~2 mm and a height of 50~250 μm. Preferably, the flow sensing electrode is located at a distance at which a sample that has not been treated with fluoride can travel within 300 ms, more preferably, within 200 ms.

The sample introducing portion enables a blood sample to be introduced into one end of the biosensor. In this case, it is preferred that the sample introducing portion be formed in the shape of an 'L', to enable the rapid, accurate and convenient introduction of the blood sample. The sample introducing portion has a structure in which an allowance space portion is formed at a location at which a sample introducing pass and an air vent are crossed. In the present specification, the term "crossed" refers to a structure in which the sample introducing pass and the air vent are crossed at one point rather than a structure in which the sample introducing pass and the air vent are arranged in parallel. The allowance space portion allows a constant and precise amount of sample to be introduced into the pass while the sample is measured, and helps an excessive amount of sample to be discharged through the air vent. Furthermore, the allowance space portion may be used as a place where the flow sensing electrode is disposed. When a blood sample is introduced into the sample introducing portion, the blood sample moves to the electrode pattern through the fine flow pass.

In the electrochemical biosensor according to the present invention, the reaction reagent layer may formed by merely applying reagent solution to only the working electrode or to both the working electrode and the flow sensing electrode. The reaction reagent layer includes an enzyme, such as a glucose oxidase or a lactate oxidase, an electron transfer mediator, a water-soluble polymer, such as a cellulose acetate, a polyvinyl alcohol or a polypyrrol, a fatty acid having 4 to 20 carbon atoms as a reagent for reducing a hematocrit effect, and a hydrophilic quaternary ammonium salt.

In the electrochemical biosensor according to the present invention, electrode connection portions, which are used to electrically connect the biosensor and the measuring device, are designed so as to be formed on a plane identical to that formed by the working electrode and auxiliary electrode connection lines, which are formed on the insulating plate in which the working electrode is provided. Blood glucose, which is measured by the biosensor of the present invention from the results of an electrochemical reaction, is provided to the measuring device through the electrode connection portions, and thus can be numerically converted into a precise blood glucose value.

The electrochemical biosensor according to the present invention includes a production lot information identification portion 500 for providing calibration curve information about liquid samples having various levels of concentration, which are used for respective production lots at the time of manufacturing the biosensor, along with biosensor production lot information, to a user.

The production lot information identification portion 500 may include one or more infrared absorption/reflection marks, which indicate information about differences between production lots through the print of colored or colorless materials having differences in the absorbency or reflectivity of infrared rays in conformity of a predetermined pattern, or through attachment of transparent films. Particularly, in the case where the transparent films are used for the infrared absorption/reflection marks and are attached, the marks are not conspicuously viewed unlike colored marks or bar codes that are conspicuous viewed, so that information about the production lots of various types of biosensors can be marked without damaging the outward appearance of the existing biosensor strip.

In this case, it is preferred that the colored or colorless materials, or the transparent films, absorb a wavelength ranging from 700 to 1100 nm.

Figure 2:
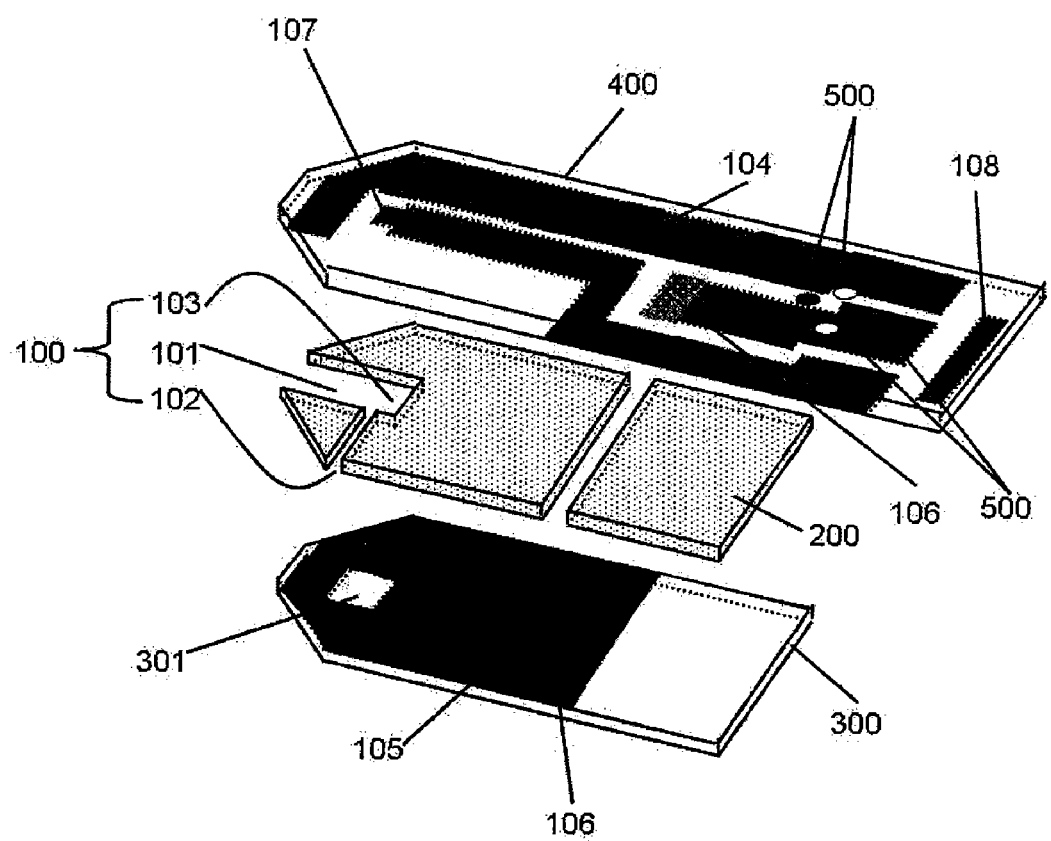
FIG. 2 is an exploded view of a biosensor, in which production lot information indicated by infrared absorption/reflection marks is recorded in the lower plate thereof, according to an embodiment of the present invention.

In the electrochemical biosensor according to the present invention, it is preferred that the number of infrared absorption/reflection marks be adjusted to fall within the range of 1 to 10. The infrared absorption/reflection marks may be located on any of an upper plate (FIG. 1) or a lower plate (FIG. 2) as long as the connections of the electrodes 104, 105, 107 and 108 and the electrode connection portions 106 are not disturbed on the biosensor.

Furthermore, the present invention provides an electrochemical biosensor measuring device quantitatively determining analytes using the electrochemical biosensor, wherein the electrochemical biosensor measuring device, comprising a plurality of integrated photo-reflector sensing devices that emit and receive reflected infrared rays in one component chip mounted on the same PCB of electrochemical measuring device to identify the infrared absorbing/reflecting production lot information recorded on the production lot information identification portion of the biosensor.

In the electrochemical biosensor measuring device according to the present invention, the operational principle of identifying the production lot information identification portion in the measuring device is described in detail below.

Figure 3:
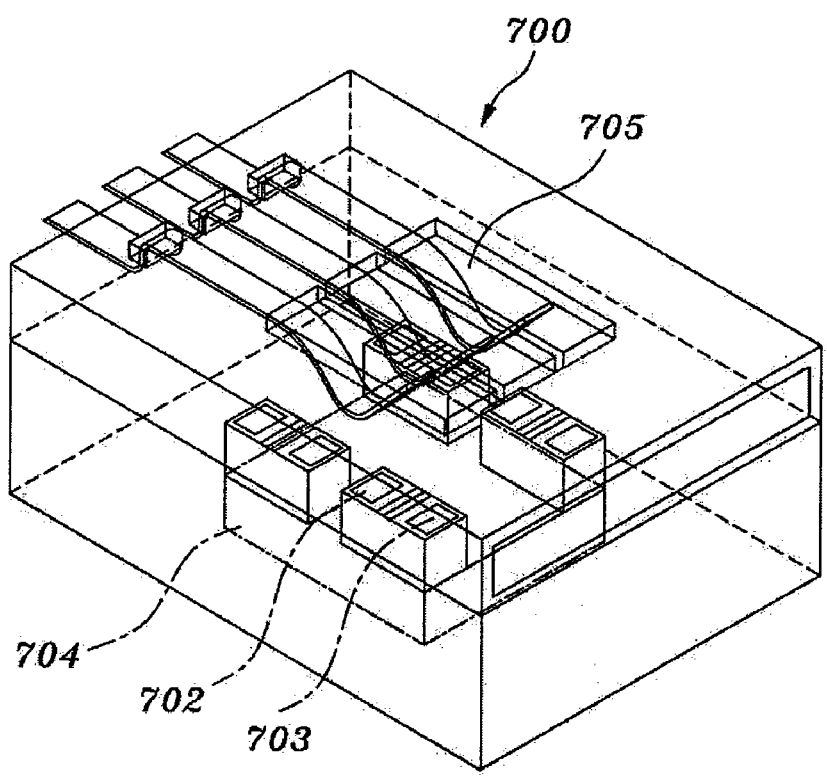
FIG. 3 is a perspective view of a biosensor measuring device, including photo-reflector sensing devices, according to an embodiment of the present invention.

In the measuring device, light-emitting units 702 and light-receiving units 703 for emitting and receiving infrared rays are arranged to be oriented to the same direction, and the surface mountable type (SMT) integrated sensing devices are attached to a Printed Circuit Board (PCB) 704 having a small area, as shown in FIG. 3. The production lot information identification portion of the biosensor is detected using the infrared rays emitted or radiated from the respective photo-reflector sensing devices. In this case, the light-emitting units 702 of the respective photo-reflector sensing devices may simultaneously or sequentially emit the infrared rays.

The infrared rays are absorbed into or reflected from the production lot information identification portion, and thus the intensities or wavelengths of infrared rays vary. The light beams reflected as described above are detected by the light-receiving unit 703, for example, photo-diodes, of the photo-reflector sensing devices. In this case, the photo-reflector sensing devices determines whether the infrared absorption/reflection marks marked on the production lot information identification portion exist, so that the infrared rays, which are emitted from the light-emitting units 702 and are sensed as production lot information, can be detected by the light-receiving units 703 without using a separate filter. Variations in the intensities and wavelengths of the infrared rays detected by the respective light-receiving units 703 are identified as digital information of 0s or 1s and are transmitted to a measuring operation device, and the measuring operation device compares the digital information with previously input production lot information, so that the production lot information of the biosensor can be identified.

In the electrochemical biosensor measuring device according to the present invention, the number of photo-reflector sensing devices is the same as that of the infrared absorption/reflection marks because infrared absorption/reflection marks corresponding to the used photo-reflector sensing devices are detected.

The production lot information identification portion marked on the electrochemical biosensor, which is used for the electrochemical biosensor measuring device according to the present invention, is not limited to a counter-type electrochemical biosensor, and may also be used for a plane type electrochemical biosensor, which is implemented such that the working electrode and the auxiliary electrode are formed on the same plate and work, and a differential type electrochemical biosensor, which is implemented such that the counter-type electrochemical biosensor and the plane type electrochemical biosensor differentially process signals.

The electrochemical biosensor measuring device according to the present invention, along with a connector having a structure in which one or more infrared absorption or reflection path(s) of light-emitting unit/production lot information identification portion/light-receiving unit can be acquired, may be used so as to identify the production lot information marked on the biosensor.

For example, the connector may be formed of a body having transparent material, such as transparent acrylic and plastic.

Furthermore, the connector may be provided with a transmission window on one side thereof so that infrared rays absorbed or reflected via the light-emitting unit/production lot information identification portion/light-receiving unit are passed therethrough. Accordingly, even when the connector is made of opaque material or even when the body of the connector has a color, the infrared rays radiated by the light-emitting units can easily reach the production lot information identification portion of the biosensor through the transmission window, and thus the production lot information can be identified.

Furthermore, in order to pass the infrared rays, which are absorbed or reflected via light-emitting unit/production lot information identification portion/light-receiving unit, through the connector, the connector may be manufactured such that one side thereof has a sliding door structure. In greater detail, when a biosensor is inserted into the connector, the sliding door structure of the connector is pushed along with the biosensor in an insertion direction of the biosensor, so that the paths of infrared rays are acquired such that the infrared rays can reach the production lot information identification portion of the biosensor. In this case, the sliding door structure may be connected to a device that can passively or automatically remove the biosensor, and thus the biosensor can be easily separated and removed from the biosensor measuring device using the removing device after the usage of the biosensor.

The photo-reflector sensing devices, which are used for the biosensor measuring device according to the present invention electrochemical, may be located inside or outside the connector of the measuring device. In greater detail, the photo-reflector sensing devices may be provided such that infrared absorption or reflection paths can be acquired in the upper or lower end portion of the connector 700 that allows the biosensor to be inserted thereinto and be connected therewith, and may be provided in the connector in a single body.

In the biosensor measuring device according to the present invention, it may be generally difficult or uneconomical to construct a system using a scheme in which an infrared absorption/reflection mark identification circuit and device are constructed in a circuit and device for measuring the biosensor of an electrochemical system. However, a system, the construction of which was considered in the past as being unreasonable due to incompatibility, can be easily and economically implemented in a narrow circuit space at the lowest cost using recently developed ultra small-sized photo-reflector technology.

For example, conventionally, for the wavelength of a light source, colored marks must be read using a filter or a monochromator, which is a kind of prism, so that the spatial limitation is great and it is difficult to construct a small-sized system. However, the identification of production lot information of the biosensor according to the present invention makes it easy to economically manufacture a device that can read one or more infrared absorption/reflection marks in the form of digital signals using ultra small-sized devices, such as photo-reflectors. A commercialized photo-reflector sensing device is very small, for example, it has a thickness of less than 2 mm and a size of 2×3 mm$^2$, so that it can be mounted, along with typical electronic devices, on the surface of a circuit board using Surface Mounted Technology (SMT), and the construction thereof is very simple and economical. In particular, the photo-reflector sensing devices, which are mounted on the top or bottom surface of the connector for electrically connecting the biosensor using the SMT, are constructed to coincide with the width of the biosensor, and thus the usage thereof is convenient. Furthermore, the photo-reflector sensing devices, along with the connector, are manufactured in a single body, and thus the construction of the biosensor measuring device can be simplified.

Furthermore, $2^n$ infrared absorption/reflection marks can be identified according to a construction method and the selection of a device, and other variable details, for example, the production time point of the biosensor, whether the product of the same manufacturer is used, and whether to be used for a specific model of device, can be recorded, including a calibrated curve for the production lots. The advantage of such electrochemical measurement is combined with the advantages of recent small-sized spectral device technologies obtained by the development of technology, and thus a biosensor that is economical and provides precise measurement values can be provided.

The production lot information identification device using photo-reflectors that sense the absorption/reflection of infrared rays in the electrochemical biosensor measuring device according to the present invention provides excellent performance and various advanced advantages when compared with conventional devices that use a colored mark identification method. Representatively, in photo-reflectors used in an infrared ray region, there is hardly a concern about abnormal operation because an interference caused by external light is too small even though optical interruption for the connector part of the measuring device is not complete. Furthermore, devices that emit infrared rays having a small energy are used, and thus very little power is consumed in contrast to devices for identifying color marks using visible rays. Accordingly, the production lot information identification device can be very appropriately used for a small-sized biosensor device. Furthermore, a circuit that enables 2-bit information to be identified using a single integrated photo-reflector sensing device and two resistors can be constructed, and thus separate amplification devices or complicated circuits are not necessary. Furthermore, information read by an infrared sensor is 2-bit signals, so that a software process of converting analog signals into digital signals is not necessary, therefore the configuration of a program is extremely simplified. The biosensor measuring device using the above-described advantages of the infrared photo-reflector sensing device hardly causes concern about abnormal operation in contrast to conventional other color identification methods or a conventional method of identifying a bar code having a complicated pattern, and thus can provide measurement results having high reliability.

Furthermore, the present invention provides a measuring method using a biosensor measuring device, including a first step of inserting a biosensor, in which a production lot information identification portion on which production lot information is recorded is provided, and causing power to be activated; a second step of identifying the production lot information of the biosensor, which is inserted at the first step, by detecting the production lot information identification portion provided in the biosensor while a plurality of photo-reflector sensing devices operates simultaneously or sequentially in the measuring device; a third step of activating measurement and operation processes of the biosensor measuring device in conformity with the production lot information identified at the second step; and a fourth step of injecting liquid sample, creating electrochemical quantitative information about the sample, a quantifying specific component of the liquid sample, and displaying quantified results.

The measuring method using a biosensor measuring device according to the present invention biosensor measuring device are described in detail according to steps below.

First, the first step is a step of inserting the biosensor, in which the production lot information identification portion on which the production lot information is recorded is provided, and causing power to be activated.

The biosensor is inserted into the measuring device through a sensor injection hole. In this case, the electrodes of the biosensor and the electrical connection portions of the connector are connected to each other, so that current flows, therefore the measuring device starts to be operated.

Next, the second step is a step of identifying the production lot information of the biosensor, which is inserted at the first step, by detecting the production lot information identification portion provided in the biosensor while a plurality of photo-reflector sensing devices operates simultaneously or sequentially in the measuring device.

When the biosensor is inserted into the connector, the biosensor and the measuring device are electrically connected to each other through the connector, and thereby the photo-reflector sensing devices in the measuring device are activated. Accordingly, the production lot information of the biosensor can be identified from the activated photo-reflector sensing devices in the form of digital signals.

The production lot information identification portion 500 may include one or more infrared absorption/reflection marks, which indicate information about differences between production lots through the print of colored or colorless materials having differences in the absorbency or reflectivity of infrared rays in conformity of a predetermined pattern, or through the attachment of transparent films. In this case, it is preferred that the number of infrared absorption/reflection marks be adjusted to fall within the range of 1 to 10.

A method of identifying the production lot information is described below.

For example, in the measuring device, light-emitting units 702 and light-receiving units 703 for emitting and receiving infrared rays are arranged to be oriented to the same direction, and the integrated photo-reflector sensing devices are attached to a Printed Circuit Board (PCB) 704 having a small area, as shown in FIG. 3. Infrared rays are emitted from the respective light-emitting unit 702 of the n photo-reflector sensing devices, and thus the production lot information identification portion of the corresponding biosensor is detected. Variations in wavelengths depending on according to the degrees of absorption or reflection of detected infrared rays are identified by photodiodes, which are the light-receiving units 703, as digital information of 0s or 1s, and thus $2^n$ pieces of data are transmitted to the measuring operation device, and the measuring operation device compares the digital information with previously input production lot information, so that the production lot information of the biosensor can be identified.

Next, the third step of a step of activating measurement and operation processes of the biosensor measuring device in conformity with the production lot information identified at the second step.

In greater detail, after the production lot information of the biosensor is identified at the second step, the measuring device causes measurement and operation processes to be activated using a calibrated curve the identified production lot information fit to the calibration curve information, and enters a standby state in which a sample can be accurately measured.

Next, the fourth step is a step of injecting liquid sample, creating electrochemical quantitative information about the sample, and quantifying a specific component of the liquid sample, and displaying quantified results.

In greater detail, a predetermined potential difference is applied between the working electrode and the auxiliary electrode and between the flow sensing electrode and the auxiliary electrode at step (b) when a liquid sample is injected into the biosensor strip inserted into the measuring device at step (a), the sample flowing into the sample introducing portion of the strip causes a primary electrical variation between the working electrode and the auxiliary electrode and, thus, the voltage between the electrodes is adjusted to be the same at step (c), the flow sensing electrode causes a secondary electrical variation by sensing the flow of the sample and the voltage between the auxiliary electrode and the flow sensing electrode is adjusted to be the same, and thus information about the time difference with the electrical variation primarily sensed by the working electrode is provided at step (d), a stationary current value, which is reached after a voltage is applied again between the working electrode and the auxiliary electrode and thereby cycling reaction is caused in a counter-type thin layer electrochemical cell, is read at step e when a liquid sample and a reagent, which is applied to the working electrode, are sufficiently mixed, the amount of substrate present in the sample is measured using the time information acquired at step d and the stationary current value acquired at step e and thus a specific component, such as blood glucose, is measured, and the result is indicated through a display window.

As described above, in accordance with the electrochemical biosensor and the biosensor measuring device according to the present invention, production lot information is recorded on the electrochemical biosensor strip using simple and convenient infrared absorption/reflection marks and is read in the form of digital signals using photo-reflector sensing devices that enable the attachment of the infrared absorption/reflection marks to the surface of a circuit board using SMT, so that large pieces of information can be identified. Furthermore, the construction thereof is very simple, and the usage of a high-priced filter and a complicated analogue-digital conversion and operation system, which are used in a conventional light-emitter and detector system, is not required, so that economic advantage can be achieved. Furthermore, the production lot information recorded on the biosensor is automatically identified, so that inconvenience and error that occur when a user personally inputs the production lot information of the biosensor can be reduced, with the result that the measured values can be conveniently and accurately acquired.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An electrochemical biosensor measuring device quantitatively determining analytes using an electrochemical biosensor, wherein the electrochemical biosensor comprises,
    a plurality of electrodes, capillary sample cell, reaction reagent layers, electrical connection portions; and
    a production lot information identification portion configured such that production lot information is recorded on at least one insulating plate;
    wherein the production lot information identification portion configured such that the production lot information is recorded thereon has infrared absorption/reflection marks, which indicate information about differences between production lots through printing of colored or colorless materials or attachment of transparent films, having differences in absorbency or reflectivity of infrared rays, in conformity of a predetermined pattern;
    wherein a number of the infrared absorption/reflection marks ranges 1 to 10; and
    wherein the electrochemical biosensor measuring device comprises a plurality of integrated photo-reflector sensing devices that emit and receive reflected infrared rays in one component chip mounted on the same PCB of the electrochemical measuring device to identify the infrared absorbing/reflecting production lot information recorded on the production lot information identification portion of the biosensor.

2. The electrochemical biosensor measuring device as set forth in claim 1, wherein the colored or colorless materials, or the transparent films, absorb light having a wavelength ranging from 700 to 1100 nm.

3. The electrochemical biosensor measuring device as set forth in claim 1, wherein a number of said integrated photo-reflector sensing devices is identical to the number of infrared absorption/reflection marks that are printed on and/or attached to the biosensor.

4. The electrochemical biosensor measuring device as set forth in claim 1, wherein the plurality of integrated photo-reflector sensing devices comprise respective light-emitting units that simultaneously or sequentially emit the infrared rays.

5. The electrochemical biosensor measuring device as set forth in claim 1, wherein the received infrared rays for the production lot information is detected by respective light-receiving units of the photo-reflector sensing devices without using separate filters.

6. The electrochemical biosensor measuring device as set forth in claim 1, wherein the reflector sensing devices are used to identify the production lot information recorded in the biosensor, together with a electrical connector having a structure in which one or more infrared absorption or reflection path(s) of light-emitting unit/production lot information identification portion/light-receiving unit, can be provided.

7. The electrochemical biosensor measuring device as set forth in claim 6, wherein the photo-reflector sensing devices are provided such that the infrared absorption or reflection paths are provided in an upper or lower end portion of the connector, which is configured such that the biosensor is inserted thereinto and is electrically connected therewith.

8. The electrochemical biosensor measuring device as set forth in claim 6, wherein the photo-reflector sensing devices are integrated such that the infrared absorption or reflection paths are provided in the connector, which is configured such that the biosensor is inserted thereinto and is electrically connected therewith.

9. A measuring method using a biosensor measuring device, comprising:
    a first step of inserting a biosensor, in which a production lot information identification portion on which production lot information is recorded is provided, and causing power to be activated;
    a second step of identifying the production lot information of the biosensor, which is inserted at the first step, by detecting the production lot information identification portion provided in the biosensor while a plurality of photo-reflector sensing devices operates simultaneously or sequentially in the measuring device;
    a third step of activating measurement and operation processes of the biosensor measuring device in conformity with the production lot information identified at the second step; and
    a fourth step of injecting liquid sample, creating electrochemical quantitative information about the sample, a quantifying specific component of the liquid sample, and displaying quantified results.

* * * * *